United States Patent

Foglio et al.

[11] 4,012,381
[45] Mar. 15, 1977

[54] PROCESS FOR PREPARING CEPHALOSPORINS AND INTERMEDIATES

[75] Inventors: Maurizio Foglio; Giovanni Franceschi; Paolo Masi; Antonino Suarato, all of Milan, Italy

[73] Assignee: Societa' Farmaceutici Italia S.p.A., Milan, Italy

[22] Filed: June 12, 1975

[21] Appl. No.: 586,376

[30] Foreign Application Priority Data
June 12, 1974 Italy .................... 23887/74

[52] U.S. Cl. .................... 260/243 C; 424/246
[51] Int. Cl.² ............. C07D 501/18; C07D 501/20
[58] Field of Search .................... 260/243 C

[56] References Cited

UNITED STATES PATENTS 3,905,965  9/1975  Martel et al. .................... 260/243 C

*Primary Examiner*—Nicholas S. Rizzo
*Attorney, Agent, or Firm*—Stevens, Davis, Miller & Mosher

[57] ABSTRACT

A process is disclosed for preparing derivatives of 7-amino-cephalosporanic acid and 7-amino-desacetoxycephalosporanic acid of structure:

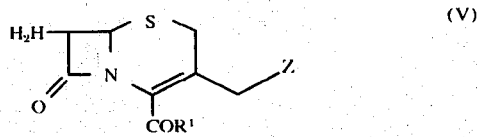

starting from a 3-acylamino-2β-thiohydrazoazetidinone of structure:

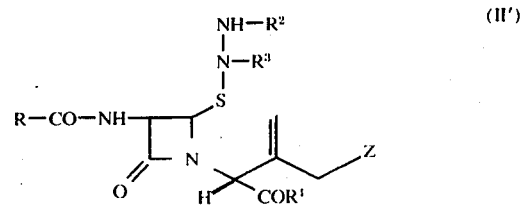

wherein the compound (II') is reacted with a phosphorous halide in the presence of a tertiary amine, the corresponding imino chloride is reacted with a lower aliphatic alcohol, the iminoether so formed is hydrolyzed with water in an acid medium, and the resultant 3-amino-2β-thiohydrazoazetidinone of structure:

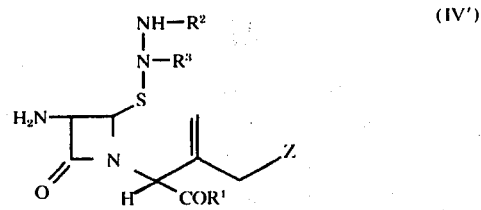

is reacted in a suitable solvent and at a temperature between −100° and +120° C with a compound selected from the class consisting of inorganic basic or weakly acid oxides and inorganic and organic bases, to finally give the desired compound (V) which is isolated and purified in known manner.

2β-thiohydrazoazetidinones are also disclosed as intermediates.

2 Claims, No Drawings

PROCESS FOR PREPARING CEPHALOSPORINS AND INTERMEDIATES

The present invention relates to a process for preparing cephalosporins and intermediates.

More particularly, the invention relates to a new process for preparing derivatives of 7-amino-cephalosporanic acid (7-ACA), of 7-aminodesacetoxy-cephalosporanic acid (7-ADCA), and of 3-amino-2-thiohydrazoazetidinones as intermediates.

Italian patent application No. 23070 A/74 (Case G.331) corresponding to U.S. application Ser. No. 578,875, filed May 19th, 1975, describes and claimed, amongst other things, 3-acylamino-2$\beta$-thiohydrazoazetidinones of structure:

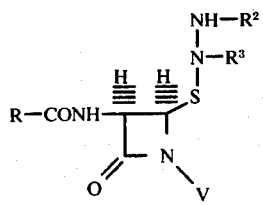

where V may be hydrogen, or an aliphatic, aromatic, arylaliphatic or acylic residue, and in particular the residues:

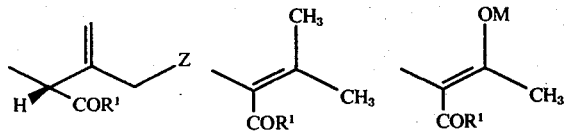

where R is selected from the class consisting of hydrogen, alkyl having from 1 to 4 carbon atoms, cyanomethyl, thienyl-methyl, furyl-methyl, naphthyl-methyl, phenyl-methyl, phenoxy-methyl, phenyl-isopropyl, phenoxy-isopropyl, pyridyl-4-thiomethyl, and tetrazolyl-1-methyl; M is hydrogen or lower alkyl.

$R^1$ is selected from the class consisting of hydroxyl, alkoxy with 1 to 4 carbon atoms, trichloro-ethoxy, benzyloxy, p-methoxybenzyloxy, p-nitrobenzyloxy, benzhydryloxy, triphenylmethoxy, phenacyloxy, and p-halophenacyloxy;

Z is selected from the class consisting of hydrogen, hydroxyl, —O—alkyl, —O—CO—alkyl, —Br, —I, —$N_3$, —$NH_2$, —O—CO—$CH_3$, O—CO—$NH_2$, and an S-mononuclear nitrogen heterocyclic ring;

$R^2$ and $R^3$ are equal or different and represent a lower alkyl, a mononuclear aryl ring, CN, a mononuclear heterocyclic ring or the radicals —$COR^4$, —$COOR^4$,

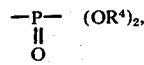

—$CONHR^4$;

or $R^2$ and $R^3$ together may represent the residues:

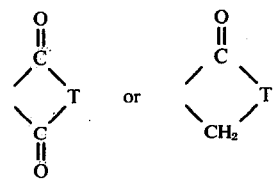

where T represents

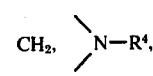

and $R^4$ is a lower alkyl, a mononuclear aryl ring or a mononuclear heterocyclic ring.

It has now surprisingly been found — and this constitutes one of the principal objects of the present invention — that said 3-acylamino-2$\beta$-thiohydrazoazetidinones (II) may be deacylated to the correspondingly 3-amino-2$\beta$-thiohydrazetidinones (IV) by successive treatment with a halogenating agent, a lower aliphatic alcohol and a hydrolyzing agent in accordance with the equation:

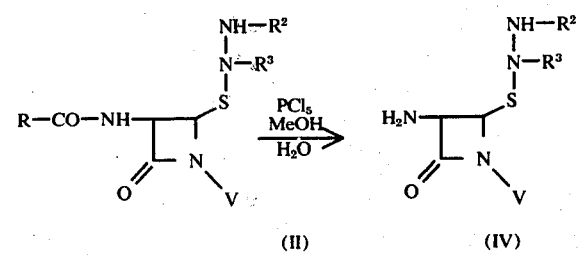

where R, $R^2$, $R^3$ and V have the meanings given above.

It has also surprisingly been found that if the said 3-amino-2$\beta$-thiohydrazoazetidinones, in which the substituent V represents the residue

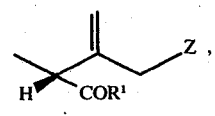

are reacted with inorganic oxides or bases, as described and claimed in Italian Patent Application No. 23070 A/74 (Case G.331) they cyclise to derivatives of 7-ACA or 7-ACDA in accordance with the equation:

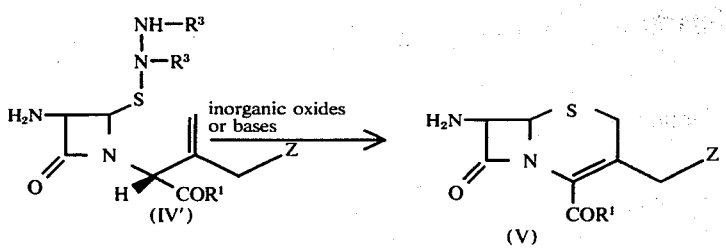

where R¹, R², R³ and Z have the meanings given above.

This process, the details of which will be described hereinafter, represents a new and surprising method for preparing derivatives of 7-amino-cephalosporanic acid (7-ACA) and of 7-amino-desacetoxycephalosporanic acid (7-ADCA), which are key intermediates for the preparation of a very wide series of cephalosporins.

A further object of the present invention is the preparation of cephalosporins of structure (III), starting from the aforementioned compounds of structure (IV'), by reacting the latter with an R—CO—X' compound to give, in a first stage, 3-acylamino-2β-thiohydrazoazetidinones of structure (II'), which when then reacted with inorganic oxides or bases in accordance with the conditions described and claimed in Italian Patent Application No. 23070 A/74 (Case G.331) finally give the cephalosporins of structure (III) in accordance with the equations:

solvent under vacuum, the residue is redissolved at 0° C in a lower aliphatic alcohol, preferably methanol, and left for some hours at room temperature. In this way the corresponding imino-ether is formed. The solvent is eliminated by evaporating to dryness and the residue is redissolved in an aqueous solvent such as tetrahydrofuran/water to hydrolyse the imino-ether to the amine (IV').

The reaction product is left at room temperature, then the solvent is evaporated under vacuum; water, sodium chloride and a solvent immiscible with water (e.g., ethyl acetate) are added and the mixture shaken.

The desired product (IV') passes entirely into the aqueous layer, from which it is extracted by slight alkalisation and extracting thoroughly with the solvent immiscible with water.

The cyclising of the intermediate (IV') to derivatives of 7-ACA or 7-ADCA (V) constitutes, as stated here-

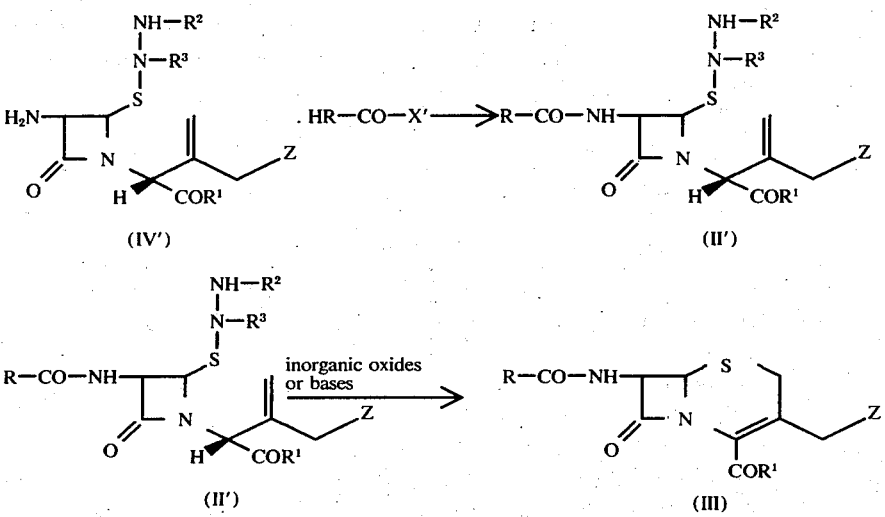

where R, R¹, R², R³ and Z have the meanings given above, and X' represents chlorine, bromine, hydroxyl, an acyloxy radical with 1 to 4 carbon atoms, or the residue

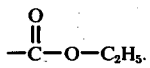

In the first step of the process according to the present invention, the 3-acylamino-2β-thiohydrazoazetidinone is converted into an imino-halide by reaction with a phosphorous halide such as phosphorus pentachloride in a suitable solvent (e.g., benzene) at a temperature between −10° C and +100° C in the presence of a tertiary amine such as pyridine. After evaporating the tofore, a new and surprising method for the practical preparation of 7-aminocephalosporanic acid and 7-amino-desacetoxy-cephalosporanic acid.

The intermediate compound (IV') is reacted in a suitable solvent (e.g., benzene) at a temperature between −100° C and +120° C with inorganic oxides such as $Al_2O_3$, $Fe_2O_3$, $Cr_2O_3$, $SiO_2$, or with inorganic or organic bases such as KOH, $Ha_2CO_3$, $NH_4OH$, alkali metal alcoholates, aliphatic, aromatic and heterocyclic amines, alkylammonium bases and basic resins. In this way, the derivative (V) is obtained, which is thereupon isolated and purified in per se known manner.

The present invention also relates to a modification of the process for preparing cephalosporins of structure (III) described and claimed in Italian Patent Application No. 23070 A/74 (Case G.331):

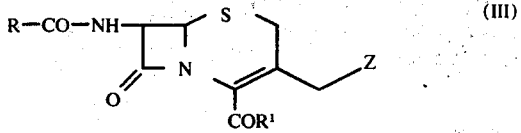

starting from a 3-amino-2β-thiohydrazoazetidinone of structure (IV') described heretofore. This is acylated on the amine group in position 3 by reaction with a compound R—CO—X' to give 3-acylamino-2-thiohydrazoazetidinones of structure (II'). These intermediates, as described and claimed in the aforementioned Italian Patent Application, are finally cyclised according to the same process as described above, i.e., by treating with inorganic oxides or bases, to give finally the cephalosporins of the said structure (III), where R, R¹, X' and Z have the meanings given above.

The following examples serve to illustrate the invention without however limiting it:

EXAMPLE 1

Methyl-2β-thiohydrazodicarboxyethyl-α-isopropenyl4-oxo-3β-amino-1-azetidine acetate.

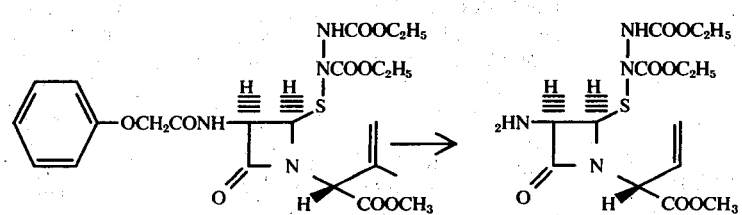

1.05 g of PCl₅ are added to a solution of 2.2 g of methyl-2β-thiohydrazodicarboxyethyl-α-isopropenyl-4-oxo-3β-phenoxyacetamido-1-azetidine acetate in 100 ml of anhydrous benzene containing 1.5 ml of anhydrous pyridine, and the whole is heated to 50° C for 60 minutes. The solvent is evaporated and the residue, cooled to 0° C, is redissolved in cold methanol, and left at room temperature for two hours. The solvent is evaporated and the residue redissolved, under cooling, in tetrahydrofuran/water (1:1, v/v), after which it is left for 30 minutes at room temperature. The tetrahydrofuran is evaporated under vacuum, whereupon salt water and ethyl acetate are added and stirring applied.

The product passes entirely into the aqueous phase, from which it is extracted by alkalizing with NaHCO₃ and extracting several times with ethyl acetate. In this way, 1.1 g of the desired product are obtained.

I.R. (CH₂Cl₂):
  3400 cm⁻¹ (NH and NH₂)
  1760 cm⁻¹ (C=O βlactam)
  1735 cm⁻¹ (C=O ester and carbamates).

EXAMPLE 2

Methyl-2β-thiohydrazodicarboxyethyl-α-isopropylidene-4-oxo-3β-amino-1-azetidine acetate.

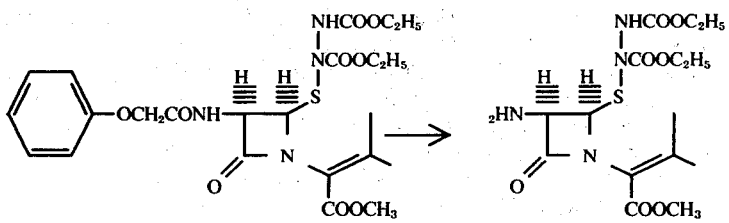

2.3 g of phosphorus pentachloride are added to a solution of 5.0 g of methyl-2β-thiohydrazodicarboxyethyl-α-isopropylidene-4-oxo-3β-phenoxyacetamido-1-azetidine acetate in 250 ml of anhydrous benzene containing 3 ml of anhydrous pyridine, and the mixture heated for 90 minutes at 50° C. The benzene is evaporated, and anhydrous methanol is added at 0° C, after which the mixture is left at room temperature for a further 90 minutes. The methanol is evaporated and a tetrahydrofuran/water mixture (1:1, v/v) is added under continuous cooling. It is left for a further 40 minutes at room temperature, the tetrahydrofuran is evaporated under vacuum, and salt water and ethyl acetate are added.

The product remains in the aqueous phase, which is alkalized with NaHCO₃ and repeatedly extracted with ethyl acetate. In this way 3.0 g of the desired product are obtained.

I.R. (CH₂Cl₂):
  3400 cm⁻¹ (NH)
  1755 cm⁻¹ (C=O βlactam)
  1725 cm⁻¹ (C=O ester and carbamates)

EXAMPLE 3

2',2',2'-trichloroethyl-2β-thiohydrazodicarboxyethyl-α-isopropenyl-4-oxo-3β-amino-1-azetidine acetate.

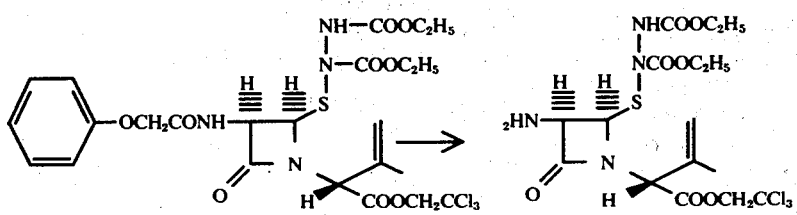 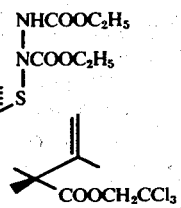

3 ml of anhydrous pyridine and 2.5 g of $PCl_5$ are added to a solution of 6.55 g of 2',2',2'-trichloroethyl-2β-thiohydrazodicarboxylethyl-α-isopropenyl-4-oxo-3β-phenoxyacetamido-1-azetidine acetate in 200 ml of anhydrous benzene, and the mixture is heated to 50° C for 90 minutes. The benzene is evaporated and anhydrous methanol is added on cooling, after which it is left at room temperature for 60 minutes. The solvent is again evaporated and the residue dissolved, after cooling, in a tetrahydrofuran/water mixture (1:1, v/v). It is left for a further 30 minutes at room temperature, the tetrahydrofuran is evaporated, and salt water and ethyl acetate are added.

The aqueous phase is separated, alkalized with $NaHCO_3$ and extracted several times with ethyl acetate to give 3.7 g of the desired product.

I.R. ($CH_2Cl_2$):
  3400 $cm^{-1}$ (NH and $NH_2$)
  1760 $cm^{-1}$ (C=O β-lactam)
  1735 $cm^{-1}$ (C=O ester and carbamates)

EXAMPLE 4

Methylester of 7-amino desacetoxycephalosporanic acid.

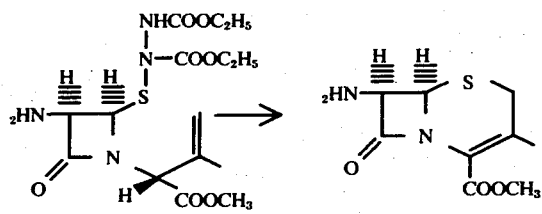

A 30% solution of KOH in water is added, under agitation in a magnetic stirrer, to a solution of 2 g of methyl-2β-thiohydrazodicarboxyethyl-α-isopropenyl-4-oxo-3β-amino-1-azetidine acetate in 100 ml of benzene, and the whole left at room temperature for 60 minutes. The organic layer is separated and washed several times with water. The product is chromatographed over silica with benzene-ethyl acetate.

In this way 0.800 g of product are obtained. m.p. 123°–124° C (ethyl ether). The product thus obtained has chemical and physical characteristics (m.p. I.R., N.M.R., mass spectrum) equal to those of a sample prepared in another manner.

EXAMPLE 5

2',2',2'-trichloroethylester of 7-aminodesacetoxycephalosporanic acid

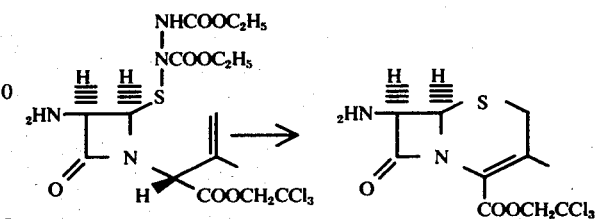

A 30% solution of KOH in water is added to a solution of 2.1 g of 2',2', 2'-trichloroethyl-2β-thiohydrazodicarboxyethylα-isopropenyl-4-oxo-3β-amino-1-azetidine acetate in 100 ml of benzene, and the mixture kept under stirring for 60 minutes. The organic layer is separated and stirred with acidified water, thus causing the product to pass into the water as salt. The organic layer is eliminated, after which the aqueous layer is alkalized with $NaHCO_3$ and then extracted with ethyl acetate.

In this way, 1.3 g of the desired product are obtained. This product coincides with the characteristics reported in the literature (J. Org. Chem. 1971, 36, 1259). Furthermore, when treated in accordance with known methods, it gave 7-amino-desacetoxycephalosporanic acid (7ADCA).

EXAMPLE 6

Methyl-2β-thiohydrazodicarboxyethyl-α-isopropylidene-4-oxo-3β-phenylacetamido-1-azetidine acetate

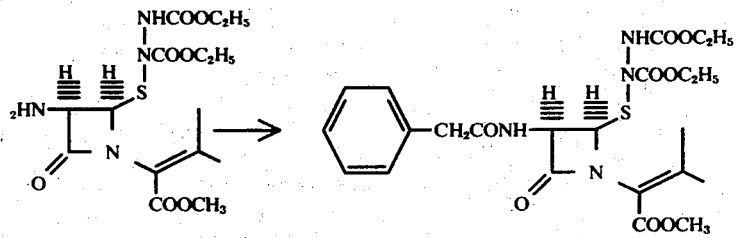

A solution of 2.0 g of methyl-2β-thiohydrazodicarboxylethyl-α-isopropylidene-4-oxo-3β-amino-1-azetidine acetate in 80 ml of benzene is combined, under stirring, with 40 ml of a saturated solution of NaHCO₃, and to this are added 1.5 ml of phenylacetyl chloride at 0° C. It is kept under stirring at room temperature for 60 minutes, and then the organic layer is separated, dried over Na₂SO₄, and evaporated. The residue is chromatographed over silica, eluting with benzene-ethyl acetate (70:30, v/v).

In this way, 2.1 g of the desired product are obtained.
IR (CHCl₃):
3420 cm⁻¹ (N-H)

1765 cm⁻¹ (C=O β-lactam)
1725 cm⁻¹ (C=O ester and carbamates)
1670 cm⁻¹ (C=O amide)
NMR (CDCl₃): 1.14 and 1.17 (two t, 6H, 2 CH₃—C(H₂)—), 2.02 and 2.19 (two s, 6 H,

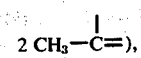
2 CH₃—C=), 3.57 (s, 2 H, C₆H₅) —CH₂—CO—), 3.67 (s, 3 H, COOCH₃), 4.08 (q, 4H, 2 CH₂—C(H₃) ), 4.88 (dd, 1 H, C(3)H), 5.70 (d, 1 H, C(4)H) and 6.5-7.4 δ (m, 7 H, 2 CONH and C₆H₅).

EXAMPLE 7
Methyl-2β-thiohydrazodicarboxyethyl-α-isopropenyl4-oxo-3β-phenylacetamido-1-azetidine acetate This is prepared in a like manner as the product of Example 6. The product obtained, when treated with bases in accordance with known manner, gave the corresponding desacetoxycephalosporin having characteristics equal to a sample prepared in another manner, as well as corresponding to the data reported in the literature. (J. Chem. Soc., 1971, 3540).

EXAMPLE 8
2′, 2′, 2′-trichloroethyl-2β-thiohydrazodicarboxyethyl-α-isopropenyl-4-oxo-3β-[N-(ter-butoxycarbonyl)-D-α-phenylglycinamido]-1-azetidine acetate

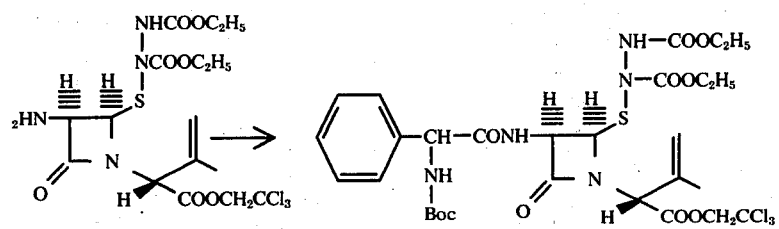

A solution of 1.1 g of carboterbutoxyphenylglycine and 0.62 m of triethylamine in 10 ml of methylene chloride are added at −15° C, under stirring, to 0.4 ml of ethylchloroformate dissolved in 10 ml of anhydrous methylene chloride. It is left for 30 minutes under these conditions. At this point a solution of 1.7 g of 2′, 2′, 2′-trichloroethyl-2β-thiohydrazodicarboxyethyl-α-isopropenyl-4-oxo-3β-amino-1-azetidine acetate in 30 ml of CH₂Cl₂ is added slowly, under stirring. The mixture is left for 3 hours at −10° C, whereupon water and CH₂Cl₂ are added. The organic layer is separated, the aqueous layer is again extracted with CH₂Cl₂, and the organic layers are dried and evaporated to give a residue which is chromatographed over silica with benzene-ethyl acetate (80:20, v/v) to give 2.1 g of the desired product. NMR (DCDl₃): 1.14 and 1.17 (two t, 6 H, 2 CH₃—C(H₂)), 1.40 (s, 9 H, —C(CH₃)₃), 1.94 (s, 3 H, CH₃—C=), 4.08 (q, 4H, 2 CH₂—C(H₃) ), 4.90

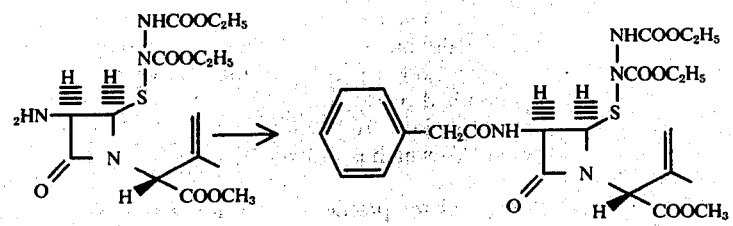

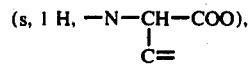

4.88 and 5.00 (2 d, 2 H, —COO—CH$_2$—CCl$_3$) 5.07 and 5.16 (widened s, 2 H, =CH$_2$), 5.28

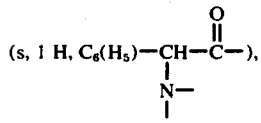

5.3 − 5.7 (m, 2 H, H of β-lactam) and 6.5 − 8.0 δ (m, 8 H; aromatic H and 3 NH).

EXAMPLE 9

2′, 2′, 2′-trichloroethyl-7-[N-(ter-butoxycarbonyl)-D-aphenyl glycinamido]-3-methyl-3-cephem-4-carboxylate.

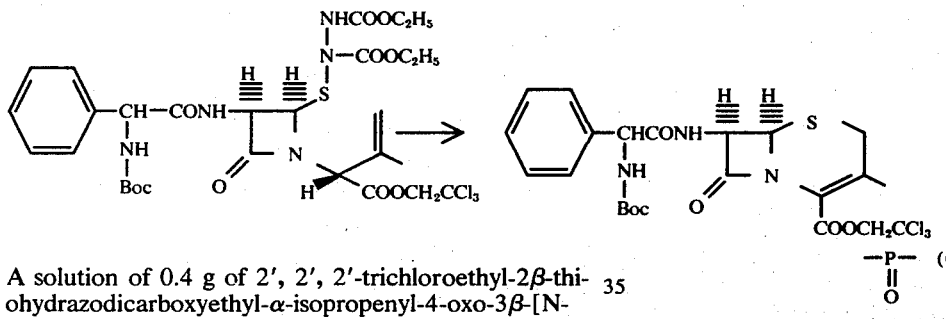

A solution of 0.4 g of 2′, 2′, 2′-trichloroethyl-2β-thiohydrazodicarboxyethyl-α-isopropenyl-4-oxo-3β-[N-(ter-butoxycarbonyl)D-α-phenylglycinamide]-1-azetidine acetate in 100 ml of benzene is kept under stirring in the presence of an excess of Al$_2$O$_3$. The mixture is left in this condition for 2 hours, after which the Al$_2$O$_3$ is filtered off and the residue is chromatographed over silica, eluting with benzene-ethyl acetate (90:10, v/v), to give 200 mg of the desired cephalosporanic product.

This product has the characteristics reported in the literature (J. Org. Chem. 1971, 36, 1259), and when treated in accordance with known methods, gave 7-(D-amino-α-phenylacetamido)-3-methyl-3-cephem-4-carboxylic acid, with the same characteristics as reported in the literature (J. Org. Chem. 1971, 36, 1259).

What is claimed is:

1. A process for preparing derivatives of 7-aminocephalosporanic acid and 7-aminodesacetoxycephalosporanic acid of structure

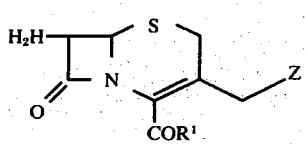

(V)

wherein R$^1$ is selected from the class consisting of hydroxyl, alkoxy having from 1 to 4 carbon atoms, trichloroethoxy, benzyloxy, p-methoxybenzyloxy, p-nitrobenzyloxy, benzhydryloxy, triphenylmethoxy, phenacyloxy, and p-halophenacyloxy;

Z is selected from the class consisting of hydrogen —O—alkyl, —O—CO—alkyl, —Br, —I, —N$_3$, —NH$_2$, —O—CO—CH$_3$, O—CO-NH$_2$ and 2-mercapto-5-methyl-1,3,4-thiadiazole;

starting from a 3-acylamino-2β-thiohydrazo-azetidinone of structure:

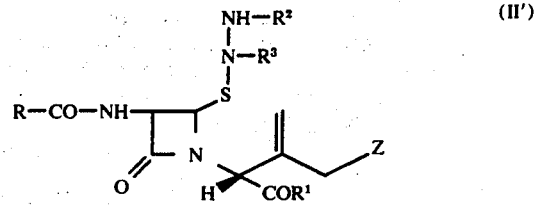

(II′)

wherein R is selected from the class consisting of hydrogen, alkyl having from 1 to 4 carbon atoms, cyano-methyl, thienylmethyl, naphthyl-methyl, phenyl-methyl, phenoxy-methyl, phenylisopropyl, phenoxy-isopropyl, pyridyl-4-thiomethyl, and tetrazolyl-1-methyl;

R$^2$ and R$^3$ are the same or different and represent -CN, or the radical —COR$^4$, —COOR$^4$, —CONHR$^4$, where R$_4$ is a lower alkyl having from 1 to 4 carbon atoms or a benzyl group;

wherein the compound (II′) is reacted with phosphorus pentachloride or phosphorus oxychloride in the presence of pyridine, the corresponding imino chloride is reacted with a lower aliphatic alcohol having from 1 to 4 carbon atoms, the imino-ether so formed is hydrolyzed with water in an acid medium, and the resultant 3-amino-2β-thiohydrazoazetidinone of structure:

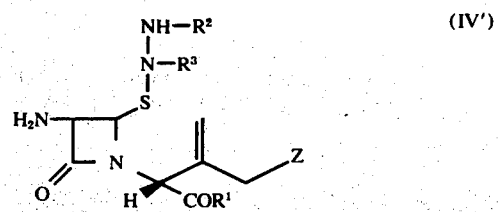

(IV′)

in which R$^1$, R$^2$, R$^3$ and Z have the meanings given heretofore, is reacted in a suitable solvent at a temperature between −100° and +120° C with an aluminum oxide or silicon oxide or with sodium, potassium or ammonium hydroxide, or a sodium, potassium or lithium alcoholate to finally give the desired compound (V) which is isolated and purified in known manner.

2. A process for preparing cephalosporins of structure (III):

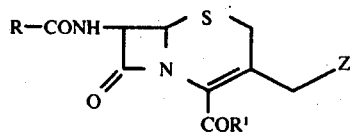 (III)

starting from a 3-amino-2β-thiohydrazoazetidinone of structure (IV'):

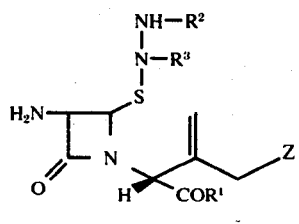 (IV')

obtained in accordance with claim 1, wherein said intermediate (IV') is reacted with a compound R—COX' to give a 3-acylamino-2β-thiohydrazoazetidinone of structure:

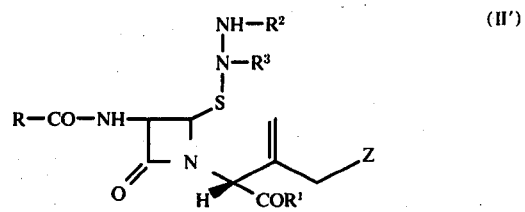 (II')

where R, $R^1$, $R^2$, $R^3$, Z have the meanings given in claim 1, and X' represents chlorine, a hydroxyl, an acyloxy radical having from 1 to 4 carbon atoms or the residue

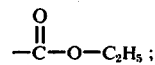

and said compound (II') is then cyclized to compound (III).

* * * * *

UNITED STATES PATENT OFFICE
CERTIFICATE OF CORRECTION

Patent No. 4,012,381                    Dated March 15, 1977

Inventor(s) Maurizio Foglio et al.                    PAGE 1 of 2

It is certified that error appears in the above-identified patent and that said Letters Patent are hereby corrected as shown below:

In the Abstract, upper left corner of formula V, for "$H_2H$" read --$H_2N$--;

Column 1, line 16, for "claimed" read --claims--;

Column 3, in the third line of the formula following line 30, for "HR—CO—X'" read --R—CO—X'--;

Column 3, line 60, insert -- -O- -- before "$\overset{\overset{O}{\|}}{C}$-O-$C_2H_5$";

Column 4, line 60, for "$Ha_2CO_3$" read --$Na_2CO_3$--;

Column 9, in the formula after line 40, insert the first portion of parenthesis after "2" and before "$CH_3$", so that the formula reads:

$$--2(CH_3—C=)--$$

UNITED STATES PATENT OFFICE
CERTIFICATE OF CORRECTION

Patent No. 4,012,381　　　　　　　Dated March 15, 1977

Inventor(s) Maurizio Foglio et al.　　　PAGE 2 of 2

It is certified that error appears in the above-identified patent and that said Letters Patent are hereby corrected as shown below:

Column 11, line 37, for "phenylglycinamide" read --phenylglycinamido--;

Column 11, line 55, upper left corner of formula V, for "$H_2H$" read --$H_2N$--;

Column 14, line 20, insert -- -O- -- before "$\overset{\overset{O}{\|}}{C}-O-C_2H_5$"

Signed and Sealed this sixteenth Day of August 1977

[SEAL]

Attest:

RUTH C. MASON
Attesting Officer

C. MARSHALL DANN
Commissioner of Patents and Trademarks